United States Patent
Struble

(10) Patent No.: US 7,058,443 B2
(45) Date of Patent: Jun. 6, 2006

(54) DIAGNOSTIC FEATURES IN BIATRIAL AND BIVENTRICULAR PACING SYSTEMS

(75) Inventor: Chester Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/842,404

(22) Filed: Apr. 26, 2001

(65) Prior Publication Data

US 2002/0183636 A1  Dec. 5, 2002

(51) Int. Cl.
*A61B 5/0402* (2006.01)
(52) U.S. Cl. .................................... 600/520
(58) Field of Classification Search ............... 600/373, 600/374, 393, 509, 510, 515, 516, 518, 519, 600/521; 607/4, 5, 7, 9, 11, 14, 15, 116, 607/119, 122, 123
See application file for complete search history.

(56) References Cited

U.S. PATENT DOCUMENTS

| | | |
|---|---|---|
| 4,316,472 A | 2/1982 | Mirowski et al. |
| 4,375,817 A | 3/1983 | Engle et al. |
| 4,379,459 A | 4/1983 | Stein |
| 4,384,585 A | 5/1983 | Zipes |
| 4,476,868 A | 10/1984 | Thompson |
| 4,556,063 A | 12/1985 | Thompson et al. |
| 4,577,633 A | 3/1986 | Berkovits et al. |
| 4,587,970 A | 5/1986 | Holley et al. |
| 4,712,555 A | 12/1987 | Thornander et al. |
| 4,726,380 A | 2/1988 | Vollmann et al. |
| 4,727,877 A | 3/1988 | Kallok |
| 4,800,883 A | 1/1989 | Winstrom |
| 4,830,006 A | 5/1989 | Haluska et al. |
| 4,880,005 A | 11/1989 | Pless et al. |
| 4,949,719 A | 8/1990 | Pless et al. |
| 4,953,551 A | 9/1990 | Mehra et al. |
| 4,958,632 A | 9/1990 | Duggan |
| 5,117,824 A | 6/1992 | Keimel et al. |
| 5,131,388 A | 7/1992 | Pless et al. |
| 5,144,949 A | 9/1992 | Olson |
| 5,158,078 A | 10/1992 | Bennett et al. |
| 5,163,427 A | 11/1992 | Keimel |
| 5,188,105 A | 2/1993 | Keimel |
| 5,199,428 A | 4/1993 | Obel et al. |
| 5,207,218 A | 5/1993 | Carpentier et al. |
| 5,269,298 A | 12/1993 | Adams et al. |

(Continued)

FOREIGN PATENT DOCUMENTS

EP  1075308 A1  2/2001

(Continued)

OTHER PUBLICATIONS

"Onset and Stability for Ventricular Tachyarrhythmia Detection in an Implantable Pacer-Cardioverter-Defibrillator" Olson et al., Computers in Cardiology, Oct. 7-10, 1986, IEEE Computer Society Press, pp. 167-170.
PCT, International Search Report, PCT/US/ 02/09895 (Mar. 29, 2002).

*Primary Examiner*—Robert E. Pezzuto
*Assistant Examiner*—Frances P. Oropeza
(74) *Attorney, Agent, or Firm*—Paul H. McDowall; Michael C. Soldner; Girma Wolde-Michael

(57) ABSTRACT

A biatrial and/or biventricular pacing system is used in a diagnostic context. By placing a pacing/sensing lead in three or four chambers of the heart, various conduction sequences can be determined and the originating chamber of various arrhythmias can be identified. This information is stored temporarily in the pacemaker until it is extracted for analysis.

18 Claims, 12 Drawing Sheets

U.S. PATENT DOCUMENTS

| | | |
|---|---|---|
| 5,312,453 A | 5/1994 | Shelton et al. |
| 5,314,430 A | 5/1994 | Bardy |
| 5,330,507 A | 7/1994 | Schwartz |
| 5,330,513 A | 7/1994 | Nichols et al. |
| 5,331,966 A | 7/1994 | Bennett et al. |
| 5,354,316 A | 10/1994 | Keimel |
| 5,545,186 A | 8/1996 | Olson et al. |
| 5,720,768 A * | 2/1998 | Verboven-Nelissen ......... 607/9 |
| 6,141,586 A * | 10/2000 | Mower ......................... 607/9 |
| 6,430,439 B1 * | 8/2002 | Wentkowski et al. .......... 607/9 |
| 6,597,951 B1 * | 7/2003 | Kadhiresan et al. ........... 607/9 |

FOREIGN PATENT DOCUMENTS

| | | |
|---|---|---|
| WO | WO9218198 | 10/1992 |
| WO | WO 9744090 A1 | 11/1997 |
| WO | WO 0057952 A1 | 10/2000 |
| WO | WO 0074552 A2 | 12/2000 |

* cited by examiner

DIAGNOSTIC FEATURES IN BIATRIAL AND BIVENTRICULAR PACING SYSTEMS

FIELD OF THE INVENTION

The present invention relates to multi-chamber cardiac pacing systems that utilize pacing/sensing leads in three or four chambers of the heart.

BACKGROUND

The heart functions by generating an electrical signal to initiate physical contractions of various portions of the heart in a specific and timed sequence. This electrical signal is generated by the sinus node in the upper right atrial wall near the base of the heart and is conducted through the upper heart chambers, i.e., the right and left atria, and causes them to contract in a synchronous manner.

These contractions force the blood contained therein into the right and left ventricles or lower heart chambers. The electrical depolarization wave then travels through and around the ventricles, triggering their contraction, which forces the blood throughout the vascular system. The contraction of the right and left ventricles proceeds in an organized fashion which optimizes emptying of the ventricular chambers.

The synchronous electrical depolarization of the atrial and ventricular chambers can be electrically sensed and displayed, and the electrical waveform is characterized by accepted convention as the "PQRST" complex. The PQRST complex includes the P-wave, corresponding to the atrial depolarization wave, the R-wave, corresponding to the ventricular depolarization wave, and the T-wave which represents the re-polarization of the cardiac cells.

Certain diseases and conduction disturbances can interfere with the natural conduction system of the heart leading to bradycardia or tachycardia of a heart chamber. In short, various chambers of the heart may be caused to contract too early or too late with respect the intended sequence. Thus, synchronicity between the contractions of the atrial chambers or of the ventricular chambers is lost and cardiac output suffers due to the timing imbalance.

Various therapies exist to treat these cardiac deficiencies and arrhythmias. The problem heretofore has been that the cardiac condition has only been diagnosed in general. That is, although the problem has been determined to exist, little additional information has been provided. Such additional information would allow for a more targeted approach to therapy, rather than utilizing the same general therapy in all cases. The problem is further complicated by the fact that these conditions may not occur continuously. Thus, a patient being closely monitored in a hospital may not have the symptoms in question during the monitoring period. Therefore, the inability to monitor and gather information about these conditions, whenever they might occur has hindered the development of targeted therapies.

Table 1 lists a patent that discloses a rate-responsive pacemaker. Unfortunately, the system described by the cited reference lacks features for sensing, recording and utilizing the data obtained through biatrio and/or biventricular pacing systems in a manner to diagnose and more fully appreciate the nature of various cardiac conditions.

TABLE 1

| U.S. Pat. No. | Inventors | Title |
|---|---|---|
| 5,330,513 | Nichols et al. | Diagnostic Function Data Storage and Telemetry Out for Rate Responsive Cardiac Pacemaker |

The patent listed in Table 1 above is hereby incorporated by reference herein in its entirety. As those of ordinary skill in the art will appreciate readily upon reading the Summary of the Invention, Detailed Description of the Preferred Embodiments and claims set forth below, the devices and methods disclosed in the patent of Table 1 may be modified advantageously by using the techniques of the present invention.

SUMMARY OF THE INVENTION

The present invention has certain objects. That is, various embodiments of the present invention provide solutions to one or more problems existing in the prior art with respect to cardiac pacing and diagnosis in general, and fully understanding and appreciating the specifics and nature of cardiac conditions in patients having implanted cardiac pacemakers in particular. Such problems include, for example, not knowing what the nature of the various conduction pathways within a patient's heart are. Specifically, not knowing or being able to readily determine if dominant abnormal pathways have developed, let alone what they are or what their particular characteristics are. Other problems include not being able to determine the specific localized origin of certain cardiac arrhythmias, thus limiting the options for treatment to more generalized approaches. This, in turn prevents specific and targeted treatments from being implemented.

Various embodiments of the present invention have the object of solving at least one of the foregoing problems. While some pacing systems have been able to sense certain conditions and monitor certain information, such approaches have generally failed to take into account to the overall mapping of specific cardiac events and conditions between the various chambers of the heart. It is therefore another object of the present invention to provide an improved apparatus and methodology for sensing cardiac events, including naturally occurring conductions, paced events, and arrhythmias is sufficient detail to determine their predominate origin and/or pathway in order to fulfill at least one of the foregoing objects.

In comparison to known implementations of cardiac pacing systems and methodologies, various embodiments of the present invention may provide one or more of the following advantages: gathering detailed information about specific parameters of various cardiac conditions and occurrences; storing this information for a period of time so as to gather a representative and illustrative sample; determining the specific pathways, frequency and dominance of cardiac conductions; determining the originating chamber for various cardiac arrhythmias; and providing this information in a manner useful to suggest of implement specific therapies.

Some embodiments of the invention include one or more of the following features: utilizing a biatrio and/or biventricular pacing system in a diagnostic capacity to determine conduction patterns and sequences. For example, the present invention provides for measuring the timing and pathways of various cardiac sequences. This can be accomplished simply by sensing or by pacing and sensing.

Another feature of the present invention is the utilization of biatrio and/or biventricular pacing systems in a diagnostic capacity to determine the origin of various arrhythmias. For example, the present invention can determine the origin of supra ventricular tachycardias, atrial flutter, atrial fibrillation, premature ventricular contractions and ventricular tachycardias, among other conditions.

Another feature of the present invention is the utilization of sensing and pacing leads in two, three or four chambers of the heart. Four-chamber sensing provides for the largest array of diagnostic capabilities. That is, a sensing lead is placed in each atrial chamber and each ventricular chamber. Data can then be obtained and recorded from each of these sensors.

In this manner, the conduction sequences of the heart can be observed over time and this data can be provided to the cardiologist. Atrial to ventricle (and vice versa), atrial to atrial, and ventricular to ventricular conduction and timing can be obtained.

In addition, by monitoring which sensor first detects a particular problem, the origin of various cardiac arrhythmias can be determined. This information will be stored within the pacemaker and provided to the medical professional through telemetry or data transmission mechanisms.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

DETAILED DESCRIPTION

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
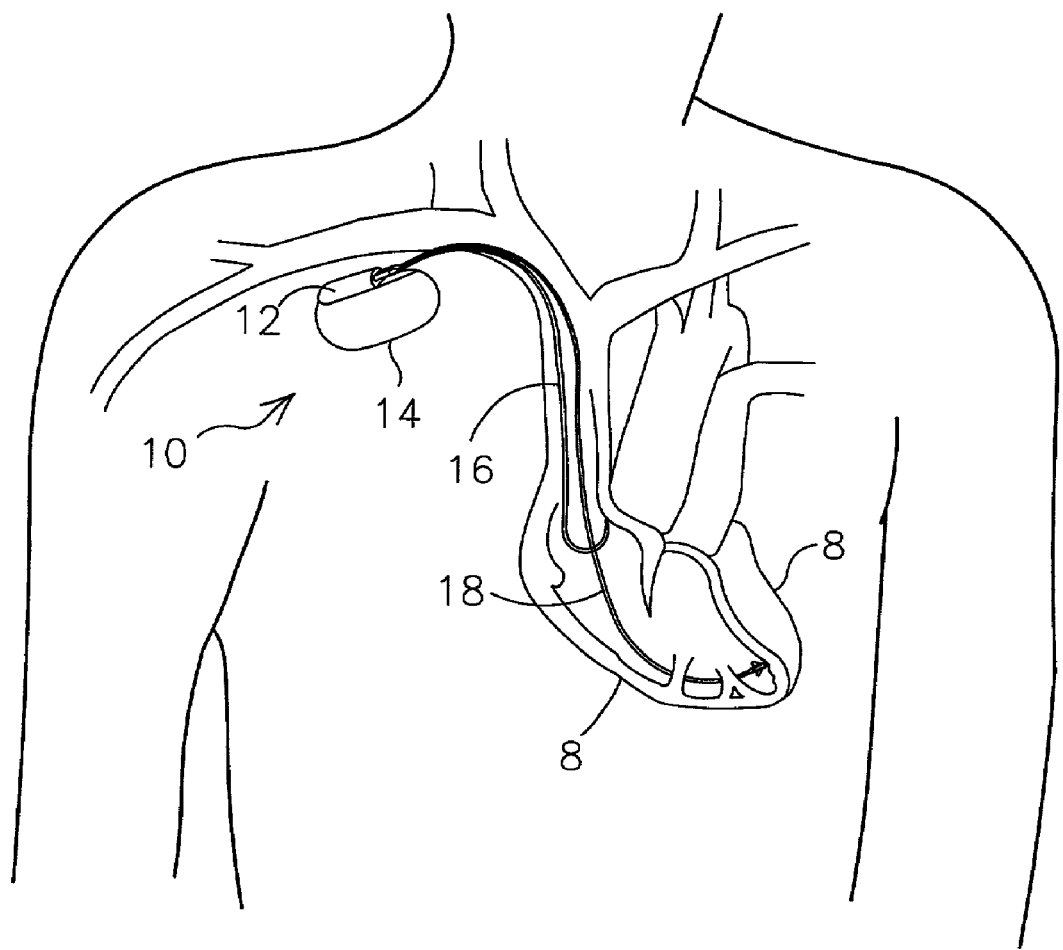
FIG. 1 is a schematic illustration of an implantable medical device within the chest cavity of a patient, adjacent to the patient's heart.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
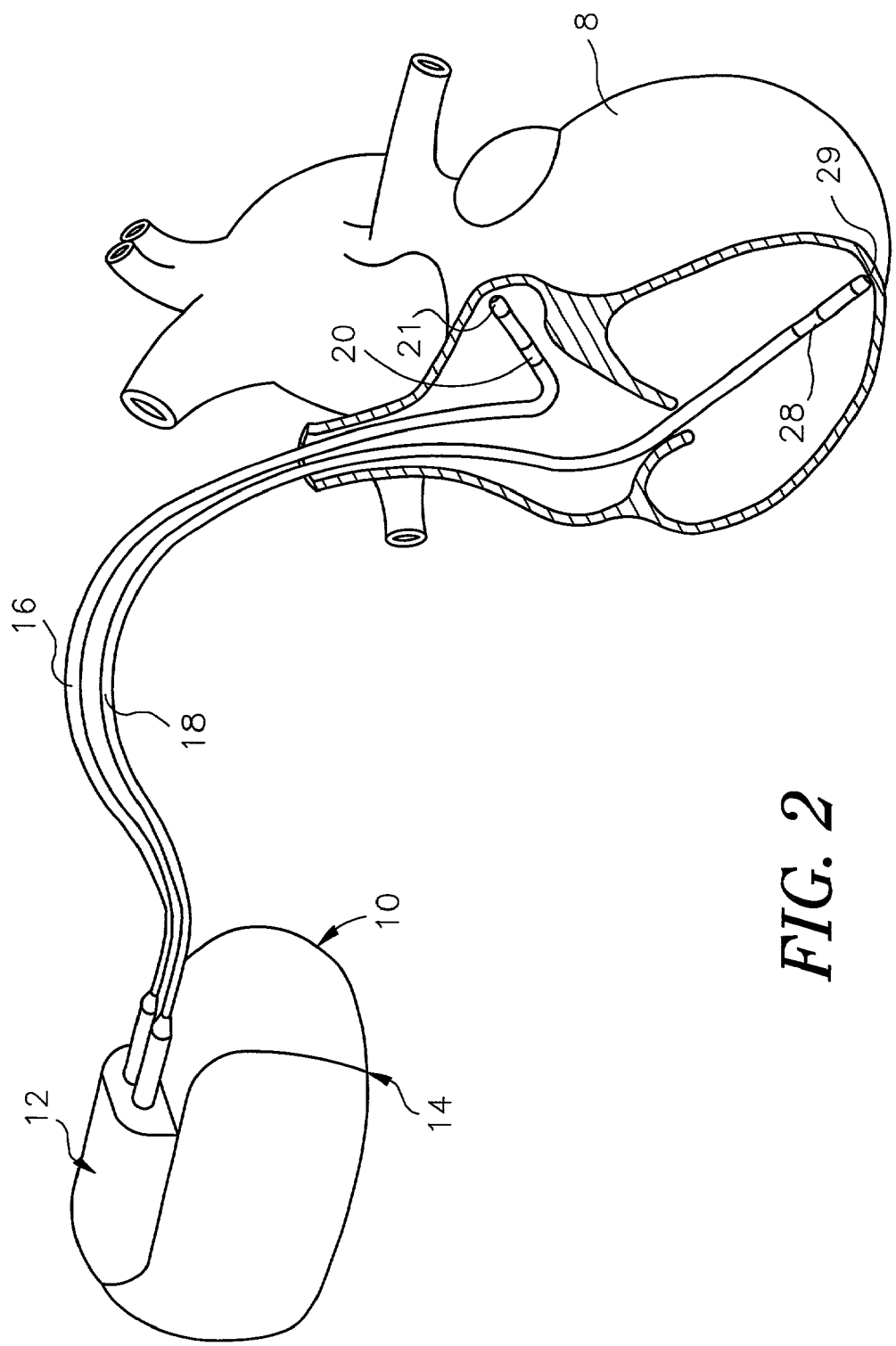
FIG. 2 is a partially sectional perspective view of an implantable medical device coupled to a mammalian heart.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
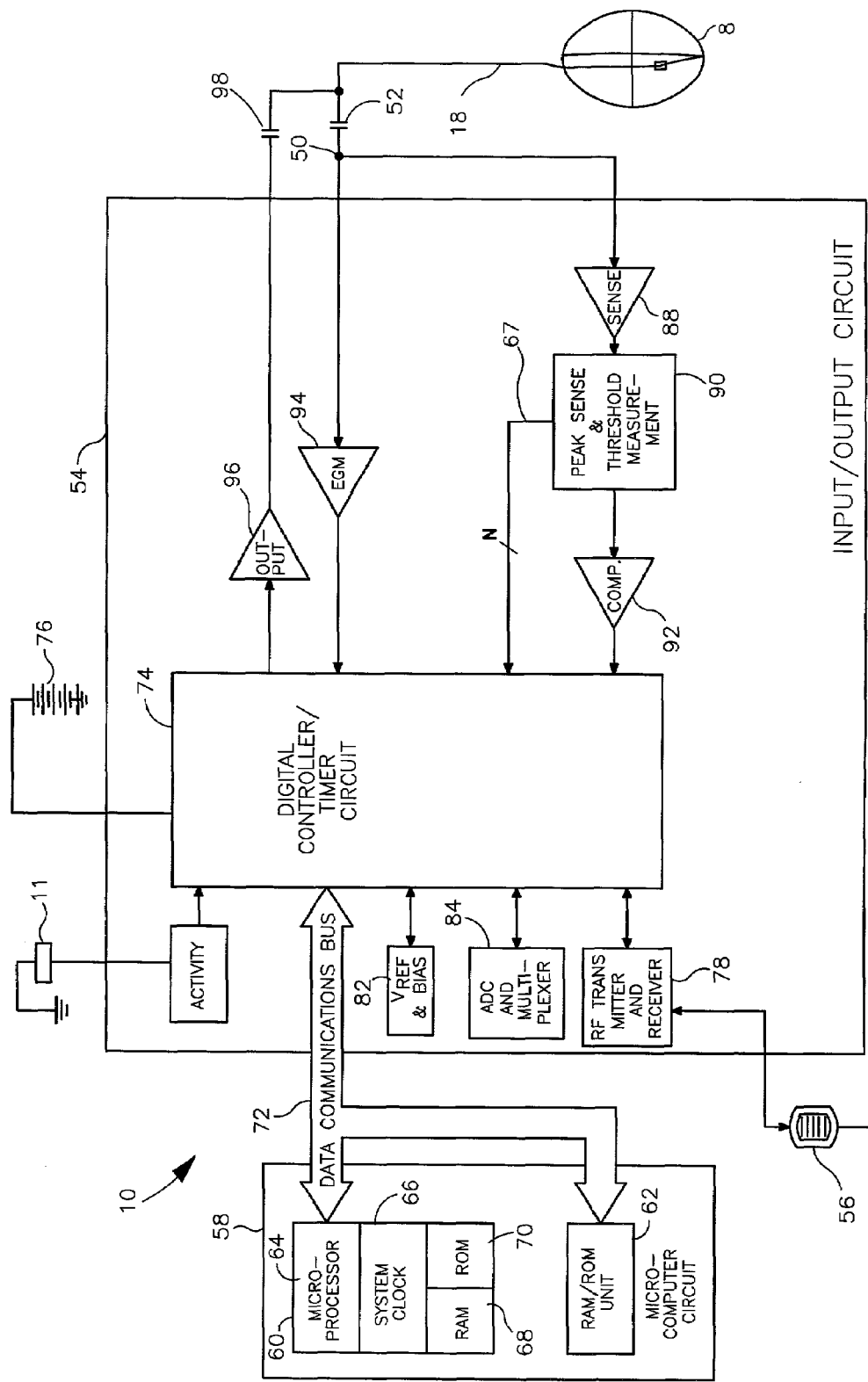
FIG. 3 is a block diagram illustrating the constituent components of an implantable medical device.

FIG. 3 shows a block diagram illustrating the constituent components of IMD 10 in accordance with one embodiment of the present invention, where IMD 10 is pacemaker having a microprocessor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output amplifier 96 may correspond generally to an output amplifier disclosed in U.S. Pat. No. 4,476,868 to Thompson, hereby incorporated by reference herein in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all hereby incorporated by reference herein, each in its respective entirety.

Figure 4:
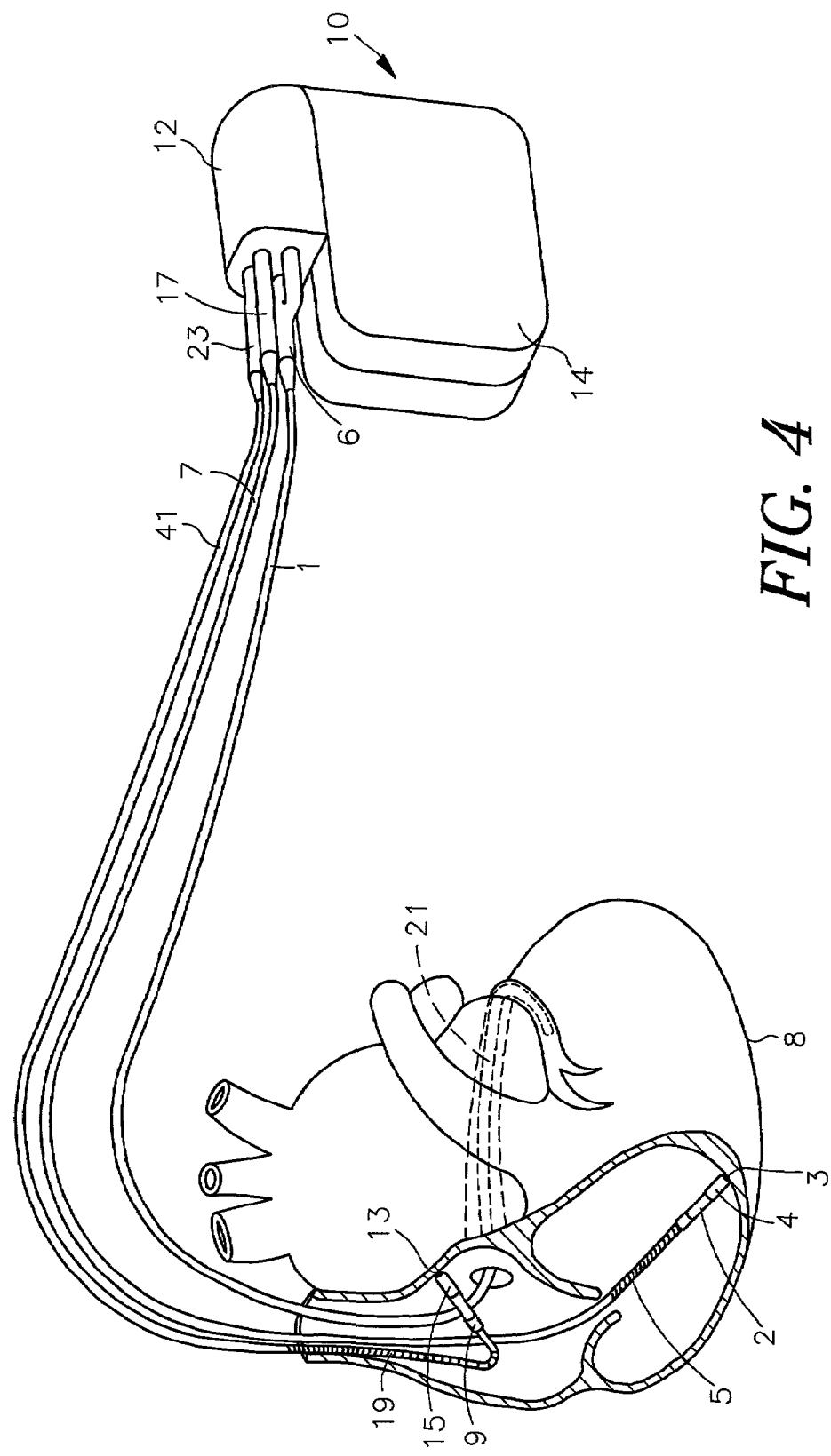
FIG. 4 is a partially sectional perspective view of a multi-lead, multi-chamber implantable medical device.
Figure 5:
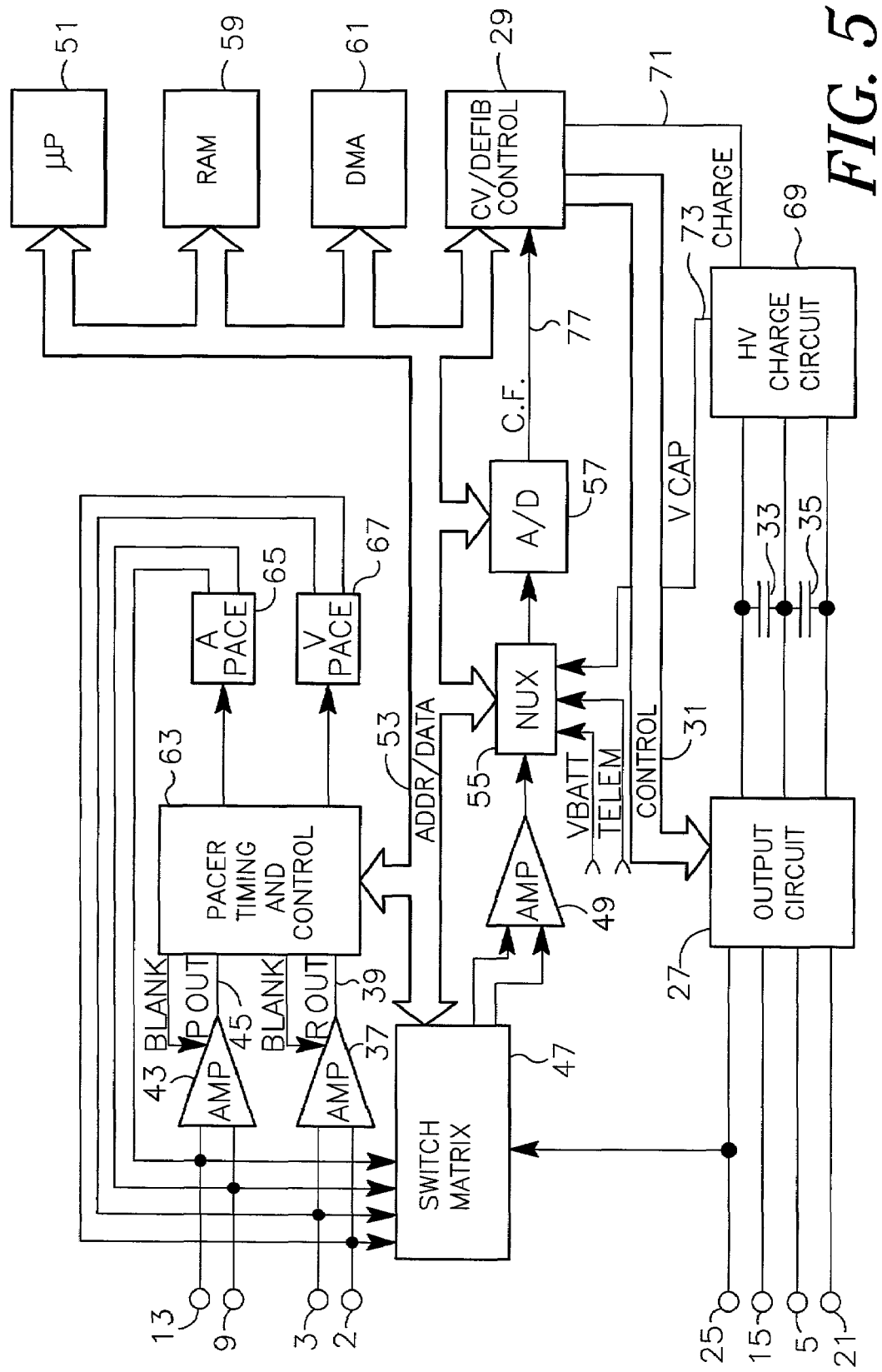
FIG. 5 is a block diagram of the constituent components of the multi-lead, multi-chamber implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. The coronary sinus/great vein electrode 41 may be about 5 cm in length.

IMD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide antitachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals", hereby incorporated by reference herein in its entirety.

Switch matrix 47 is used to select which of the available electrodes are coupled to wide band (0.5–200 Hz) amplifier 49 for use in digital signal analysis. Selection of electrodes is controlled by the microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude of the cardiac pacing pulses under control of microprocessor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al. and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, IEEE Computer Society Press, pages 167–170, also incorporated by reference herein in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May–June, 1984, pp. 541–547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
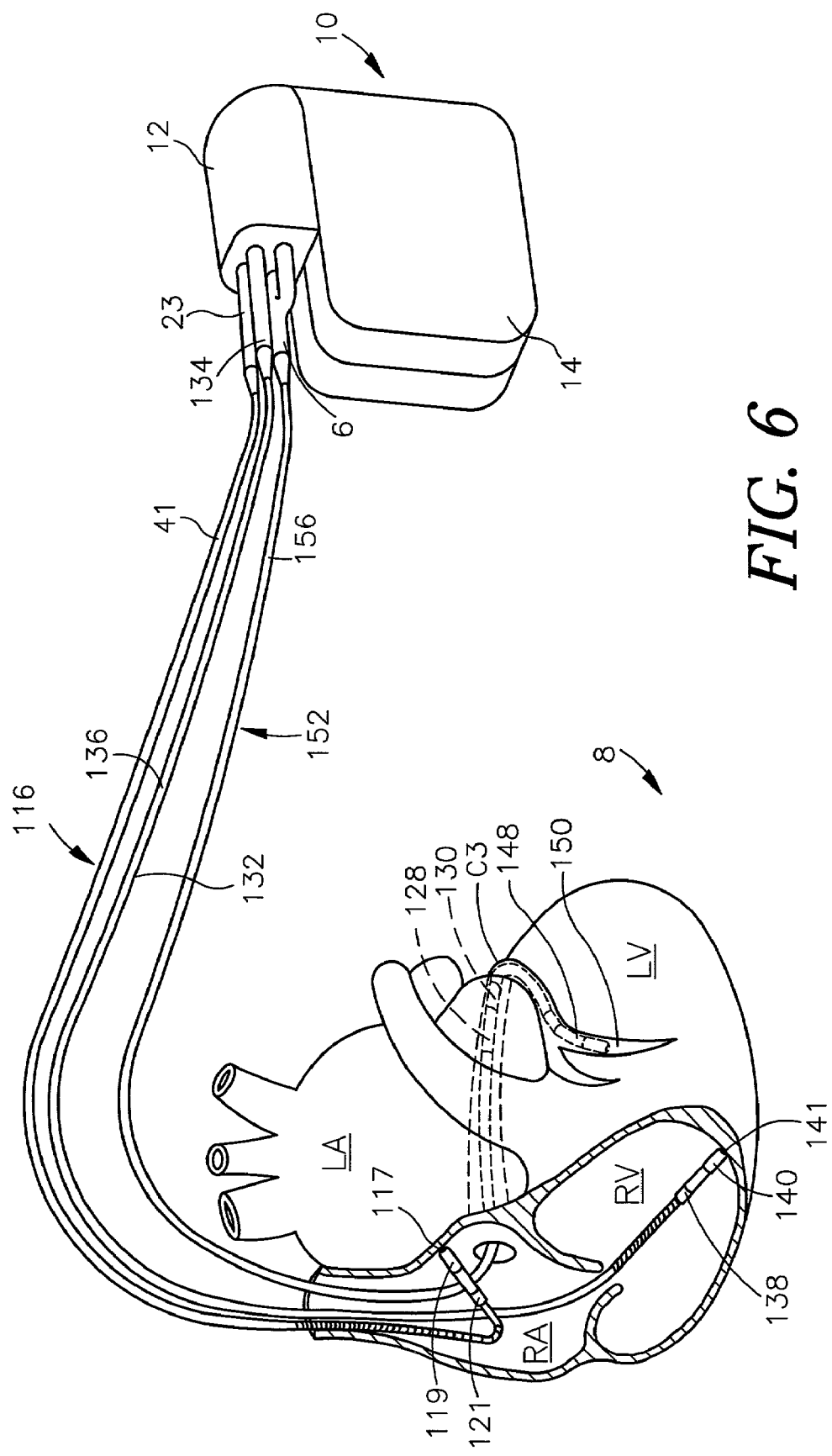
FIG. 6 is a schematic diagram illustrating a four-channel, biatrial/biventricular pacing system.

FIG. 6 is a schematic representation of an implanted, four channel cardiac pacemaker for restoring synchronous contractions of the right and left atria and the right and left ventricles. IMD 10 as illustrated in FIG. 6 in similar in structure to that illustrated in FIG. 4. IMD 10 includes an in-line connector plug 23 of right atrium (RA) lead 116 that is fitted into a bipolar bore of connector block 12 and is coupled to a pair of electrically insulated conductors within lead body 41 that are connected with distal tip RA pace/sense electrode 119 and proximal ring RA pace/sense electrode 121. The distal end of the RA lead 116 is attached to the RA wall by a conventional attachment mechanism 117. Bipolar, endocardial right ventricle (RV) lead 132 is passed through the vein into the RA chamber of the heart 8 and into the RV where its distal ring and tip RV pace/sense electrodes 138 and 140 are fixed in place in the apex by a conventional distal attachment mechanism 141. The RV lead 132 is formed with an in-line connector 134 fitting into a bipolar bore of connector block 12 that is coupled to a pair of electrically insulated conductors within lead body 136 and connected with distal tip RV pace/sense electrode 140 and proximal ring RV pace/sense electrode 138.

In this case, a quadripolar, endocardial left ventricle (LV) coronary sinus (CS) lead 152 is passed through a vein into the RA chamber of the heart 8, into the CS and then inferiorly in the great vein to extend the distal pair of LV CS pace/sense electrodes 148 and 150 alongside the LV chamber and leave the proximal pair of left atrium (LA) CS pace/sense electrodes 128 and 130 adjacent the LA. The LV CS lead 152 is formed with a four conductor lead body 156 coupled at the proximal end to a bifurcated in-line connector 6 fitting into a pair of bipolar bores of connector block 12. The four electrically insulated lead conductors in LV CS lead body 156 are separately connected with one of the distal pair of LV CS pace/sense electrodes 148 and 150 and the proximal pair of LA CS pace/sense electrodes 128 and 130.

FIG. 6 is a schematic diagram illustrating IMD 10 as a four-channel, biatrial/biventricular pacing system. The four-channel pacing system illustrated in FIG. 6 or various other three or four-channel pacing systems can be utilized with the present invention. In general, the present invention encompasses sensing events in both atrial and/or both ventricular chambers. This data is then recorded in a suitable memory device, such as random access memory 59. The data may then be exported after a certain period of time (i.e., gathering data over time) or on a real-time basis, e.g., via radio frequency telemetry. This data may then be used to aid the cardiologist in further diagnosing various cardiac conditions.

The following examples present types of data that may be collected and ways of analyzing that data to achieve a useful purpose. It is to be understood that this is not an exhaustive list of the conditions that may be diagnosed, the parameters that may be sensed or the determinations that are made. Data obtained from the pacing system can be organized in various ways. For purposes of illustration, the following examples illustrate data collected over a period of time and presented in various histogram formats. Various other data presentation and modeling techniques may be used equally well.

Figure 7:
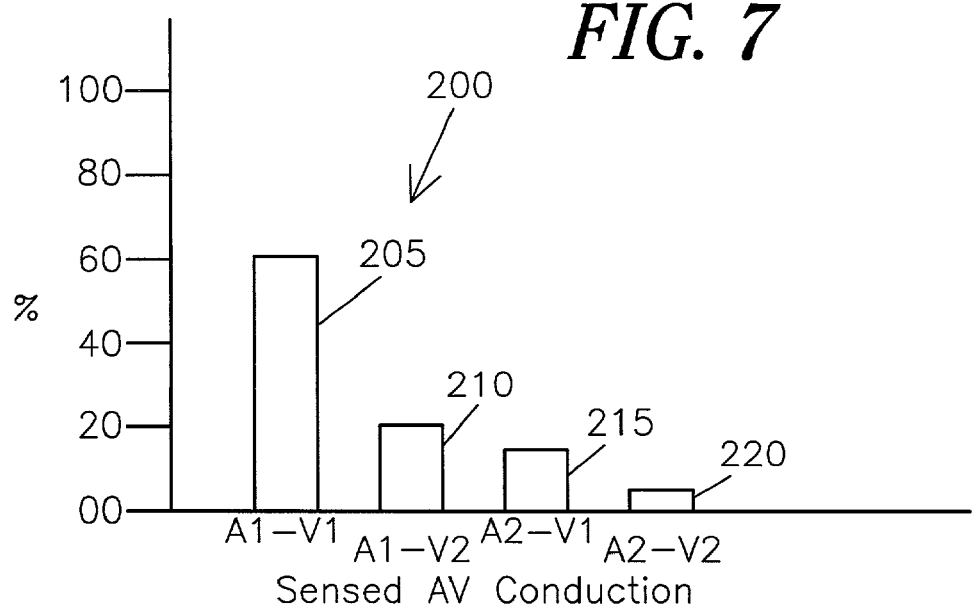
FIG. 7 is a sample histogram illustrating sensed AV conduction by the pacing system illustrated in FIG. 5.

FIG. 7 is a sample histogram 200 representing sensed AV conduction across multiple chambers. More specifically, histogram 200 represents the number of conduction sequences occurring for a given pathway over the period of time data collection occurs. Bar 205 indicates that 60% of the detected conduction sequences went from the right atrium (A1) to the right ventricle (V1). Bar 210 indicates that 20% of the conduction sequences went from the right atrium (A1) to the left ventricle (V2). Bar 215 indicates that 15% of the conduction sequences went from the left atrium (A2) to the right ventricle (V1), while bar 220 indicates that 5% of the conduction sequences went from the left atrium (A2) to the left ventricle (V2).

This data is obtained through the placement of a lead in each of the right atrium, the left atrium, the right ventricle and the left ventricle. Each event sensed by these leads can be recorded. By comparing the timing of the various events sensed, the conduction pathway can be determined. For example, for A1–V1 sensing, the right atrial lead will sense an event which is later followed by an event being sensed in the right ventricle.

From this data, the cardiologist and/or IMD 10 can determine which pathway is the dominant pathway and the major direction of conductions. Thus, the present invention is useful in diagnosing and defining various conductive disorders, based on what would be an expected conduction sequence for a healthy heart. Of course, the pacemaker would normally only have been implanted in a patient already suffering some cardiac abnormality. This data can either further define the known cardiac condition, or if the pacemaker were implanted for a different reason, identify another condition. In either case, blockages and abnormalities in conductive pathways can now be specifically identified. The therapy delivered to the patient can then be specifically tailored based on the obtained information. For example, the four-channel pacing system can be programmed to account for specific pathways that are blocked in order to achieve a normal rhythm.

More specifically, in a healthy heart one would expect a close distribution (near 50/50) between A1–V1 and A1–V2, as they should be occurring at approximately the same time. When the data indicates some predominance (as illustrated in FIG. 7), the cardiologist can determine that one of the conduction pathways is lagging behind the other. Furthermore, the significant presence of A2–V1 or A2–V2 conductions also indicates a problem or blockage in the primary conductive pathways. Once such a problem has been identified, pacing therapy can be tailored to overcome the problem. That is, the timing of the pacing can be modified so as to stimulate the lagging ventricle more frequently in order to avoid the conduction deficiency. The localization of the problem through the above data allows for a determination of the best chamber to implement the therapy. The therapy can be determined by a cardiologist observing the data, or automatically implemented by IMD 10, once the problem has been appropriately identified.

Figure 8A:
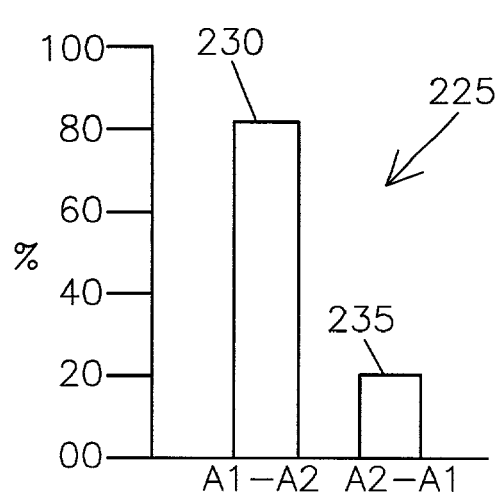
FIG. 8A is a sample histogram illustrating sensed A—A conduction by the pacing system illustrated in FIG. 5.

FIG. 8A is a sample histogram 225 representing sensed atrial conductions. That is, conductions occurring from the right atrium (A1) to the left atrium (A2) can be sensed and vice versa. The histogram simply represents the percentage occurring in one direction versus the other. Bar 230 illustrates the A1–A2 conductions representing 80% of the sensed conductions, while bar 235 illustrates the A2–A1 conductions representing 20% of the sensed conductions.

Normally, this distribution should indicate nearly all A1–A2 conductions. A significant percentage of A2–A1 conductions is indicative of an atrial arrhythmia or an ectopic focus in the left atrium which is functioning as a primary pacemaker, and thus initiating conductions occurring in a direction opposite to that desired. To perform an appropriate therapy, it is desirable to have more information regarding the timing of the conductions as discussed with reference to FIG. 8B.

Figure 8B:
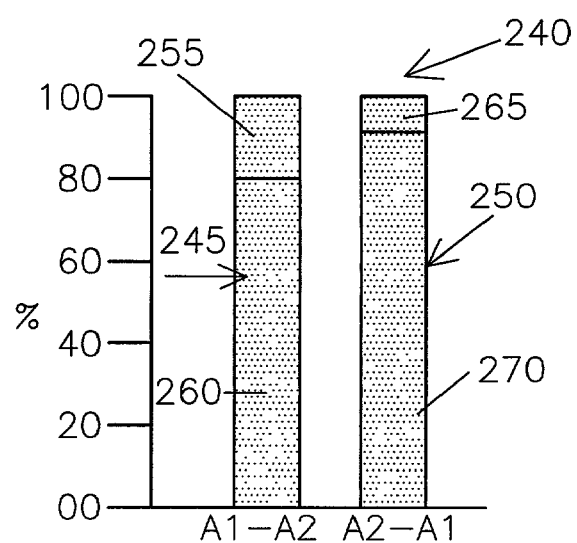
FIG. 8B is a sample histogram illustrating sensed A—A conduction that is categorized by timing intervals, as sensed by a pacing system similar to that shown in FIG. 5.

FIG. 8B also presents a sample histogram 240 indicating sensed A-A conductions. However, histogram 240 provides additional timing data. That is, the data is further broken down into timing ranges. The number and specifics of the timing ranges can be programmed as desired. By way of example, FIG. 8B illustrates conductions occurring in less than 80 ms (blocks 255, 265) and conductions taking longer that 80 ms (blocks 260, 270). Bar 245 represents the sum total of A1–A2 conductions and indicates that 80% (block 260) took longer than 80 ms, while 20% (block 255) took less than 80 ms.

Similarly, bar 250 represents the sum total of A2–A1 conductions. Block 265 indicates that 8% of the conductions took less that 80 ms, while 92% took longer than 80 ms. It should be appreciated that the illustrated histograms are simply one way of presenting the gathered data. It is the data itself, the ability to gather and store that data, and the ability to extract and utilize the data that is important. As indicated above, multiple time ranges could be established to further indicate the timing of the conductions.

Once the timing of the atrial arrhythmia or ectopic focus has been determined, the appropriate therapy can be initiated. To overcome these problems, the atrium is paced at a higher rate (or overdriven) than that determined, in order to establish the proper direction of conduction and regain proper pacemaking performance. Overdrive pacing is well known and is referred to as antitachycardia pacing (ATP). The localization of the problem through the above data allows for a determination of the best chamber to implement the therapy. The therapy can be determined by a cardiologist observing the data, or automatically implemented by IMD 10, once the problem has been appropriately identified.

Figure 9A:
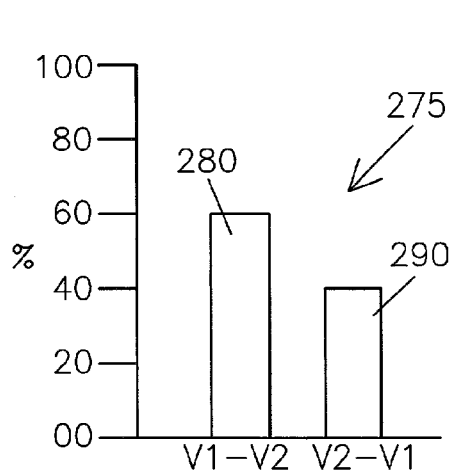
FIG. 9A is a sample histogram illustrating sensed V—V conduction by the pacing system illustrated in FIG. 5.
Figure 9B:
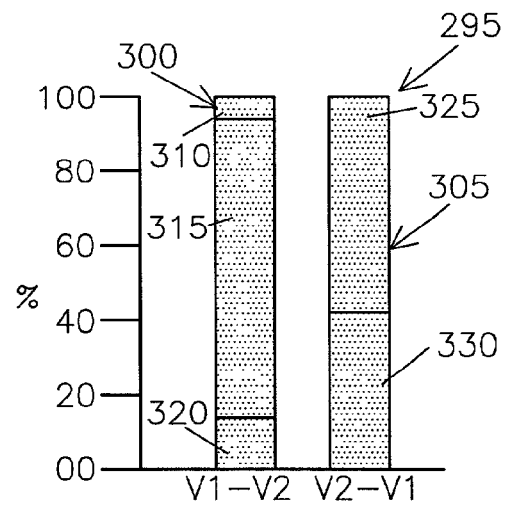
FIG. 9B is a sample histogram illustrating sensed V—V conduction that is categorized by timing intervals, as sensed by a pacing system similar to that shown in FIG. 5.

FIGS. 9A and 9B are similar to 8A and 8B, except that they illustrate histograms 275, 295 that represent conductions occurring from the right ventricle (V1) to the left ventricle (V2) and vice versa. Histogram 275 in FIG. 9A represents the percentage of conductions occurring from V1–V2 (bar 280) versus those traveling from V2–V1 (bar 290).

FIG. 9B represents additional data that categorizes the conductions based on established time ranges. In this example, three time ranges are provided:
Hatched lines=<60 ms
Shaded=60 ms–100 ms
Checkered=>100 ms.

Thus, bar 300 represents the sample V1–V2 conductions. Bar 310 indicates that 8% of the conductions in that direction take less that 60 ms. Bar 315 indicates that 80% of the conductions take between 60–100 ms and bar 320 indicates that 12% take greater than 100 ms. Similarly, bar 295 indicates the breakdown for the V2–V1 conductions. Bar 325 indicates that 60% of the conductions took between 60–100 ms and bar 330 indicates that 40% took greater than 100 ms. In this sample, there were no V2–V1 conductions that fell into the less than 60 ms time range. This data will indicate the primary conductive pathways and the relative timing involved and can indicate the interventricular conduction delay (IVCD). Again, this data is merely illustrative and more time ranges could be accommodated to further isolate the conduction patterns. This data is helpful in that once the conductive disorders are fully understood for a given patient, the appropriate therapy can be tailored.

One would normally expect that the primary conduction sequence would be V1–V2 nearly 100% of the time. Thus, deviations from this norm indicate an arrhythmia or ectopic focus. The therapy would again be the implementation of ATP to regain control of the pacemaking function. The localization of the problem through the above data allows for a determination of the best chamber to implement the therapy. The therapy can be determined by a cardiologist observing the data, or automatically implemented by IMD 10, once the problem has been appropriately identified.

Figure 10A:
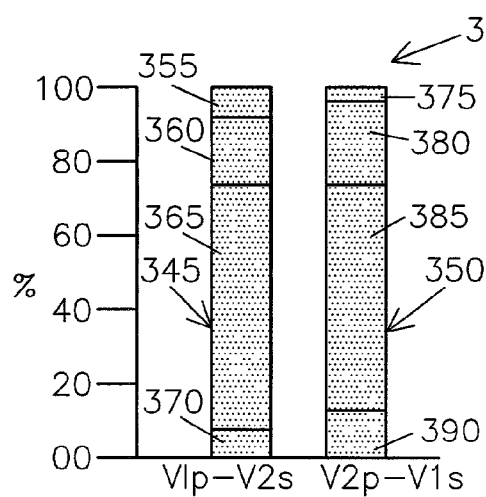
FIGS. 10A and 10B are sample histograms illustrating paced V—V conduction and paced and sensed by the pacing system illustrated in FIG. 5.
Figure 10B:
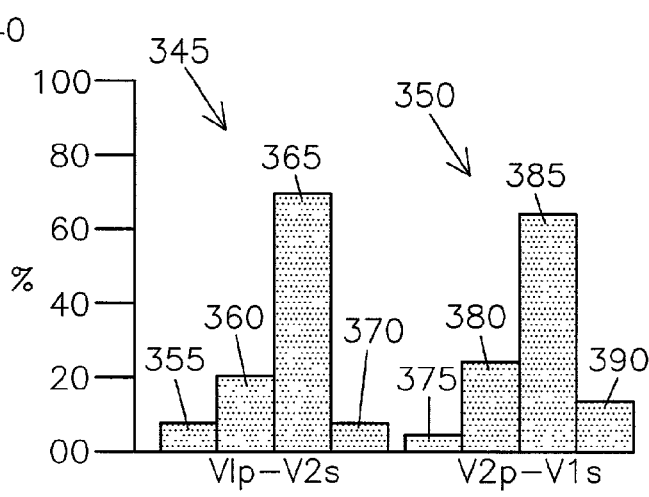

FIGS. 10A and 10B present the same data in two different formats. The data presented represents paced conduction across the ventricular chambers. That is, a pacing signal is initiated in the right ventricle V1$p$ and then sensed in the left ventricle V2$s$, or vice versa. The time between pacing and sensing is monitored and each data point is then stored in the appropriate timing bin. For this example, the timing break down is as follows:
Hatched lines=<100 ms
Shaded=100–150 ms
Checkered=150–180 ms
Vertical lines=>180 ms Thus, histogram 340 provides bar 345 that indicates the breakdown when the right ventricle (V1p) is paced and the left ventricle senses (V2s). Block 355 indicates that 8% of the conductions took less than 100 ms; block 360 indicates that 16% took between 100–150 ms; block 365 indicates that 68% took between 150–180 ms; and block 370 indicates that 8% took longer than 180 ms. Bar 350 has blocks 375, 380, 385, and 390, respectively, corresponding to the same time ranges and illustrating their respective percentages. Histogram 345 provides the exact same data in a split bar graph.

By measuring the conduction delay in this manner, the predominant interventricular conduction delay (IVCD) can be determined. The number and values of the time ranges can be set as desired in order to give the level of specificity required. Though not separately shown, other paced/sensed data collection protocols could be established. For example, pacing in an atrial chamber could be monitored in a ventricular chamber.

FIGS. 10A and 10B will indicate the timing of a conduction in a specific direction. In other words, the delay, both electrical and mechanical in nature, can be determined in each direction. This will indicate if V1 and V2 are asynchronous. Thus, if conductions in one direction are determined to be too slow, the appropriate therapy will be to pace in the other direction. This is particularly useful data in biventricular pacing where both sides can be stimulated simultaneously in order to achieve cardiac resynchronization. The therapy can be determined by a cardiologist observing the data, or automatically implemented by IMD 10, once the problem has been appropriately identified.

Figure 11A:
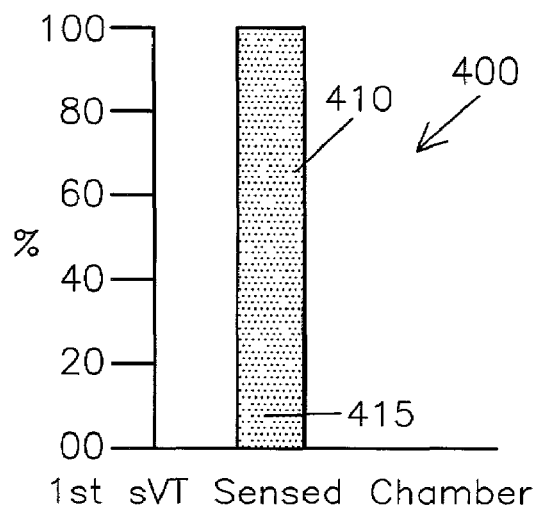
FIGS. 11A and 11B are sample histograms illustrating a determination of the origin of supra ventricular tachycardias.
Figure 11B:
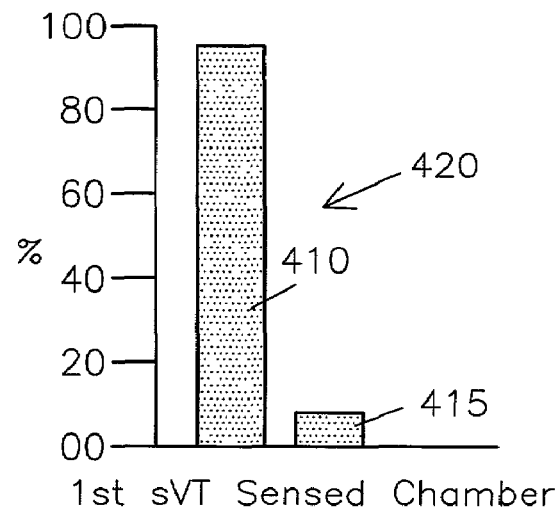

FIGS. 11A and 11B represent sample data collected by the present invention to indicate the origin of supra ventricular tachycardia (sVT) in a patient having the condition and having a biatrial pacing/sensing system implanted. In this case, both atrial leads are capable of sensing. When a sVT is detected, it is noted which atrial lead first senses it. That data is then recorded and over time, histograms 400 and 420 (both illustrating the same data in different ways) can be generated.

For this example, the sVT break down is as follows:
Bar 410=First Sensed in Right Atrium (A1)
Bar 415=First Sensed in Left Atrium (A2)

In FIGS. 11A and 11B, bar 410 represents the sVT's first sensed by the right atrial lead (A1), which in this example represent 92% of the occurrences. Bar 415 indicates that 8% of the sVT's were first sensed by the left atrial lead (A2). Thus, it becomes apparent that in this case the sVT's are predominantly being initiated in the right atrium. Thus, the implanted pacemaker can be configured to optimally recognize and treat this condition or alternative therapies could likewise be optimized.

The data will indicate which chamber the problem is occurring most frequently in. Thus, the appropriate therapy will be to implement ATP. Ideally, with biatrial pacing, ATP will be performed in the chamber initiating the problem. The localization of the problem through the above data allows for a determination of the best chamber to implement the therapy. Additional information (not separately shown) would be useful in this therapy. That is, the frequency or rate of the sVT can be determined through the collection of timing data. This will indicate at what rate IMD 10 needs to overdrive the cardiac pacing system. The therapy can be determined by a cardiologist observing the data, or automatically implemented by IMD 10, once the problem has been appropriately identified.

Figure 12A:
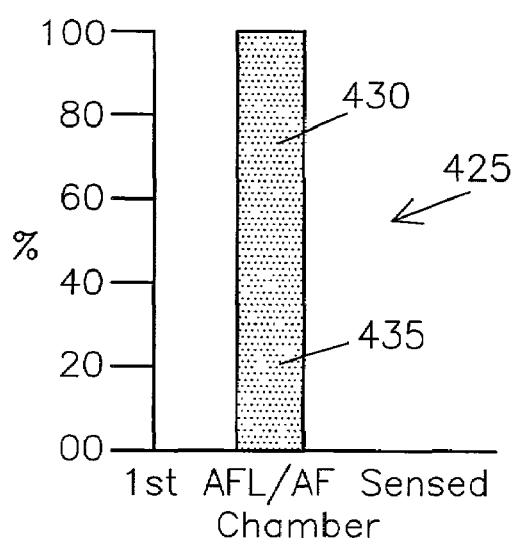
FIGS. 12A and 12B are sample histograms illustrating a determination of the origin of atrial flutter or atrial fibrillation.
Figure 12B:
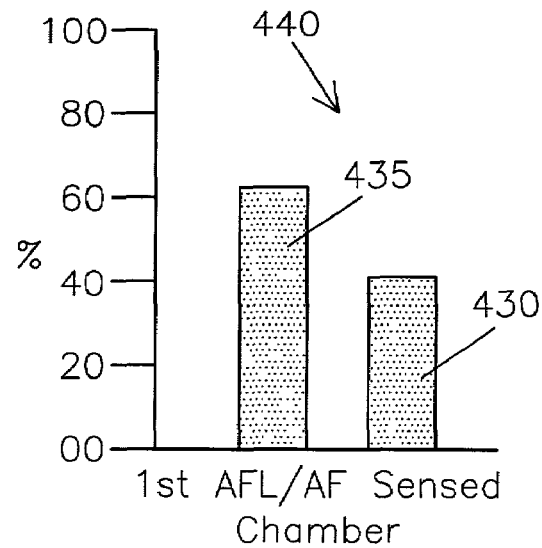

In a similar fashion, the origin of various other atrial arrhythmias can be determined. FIGS. 12A and 12B, the originating chamber of atrial flutter (AFL) or atrial fibrillation (AF) is determined. For this example, the sensed AFL/AF break down is as follows:
Bar 430=First Sensed in Right Atrium (A1)
Bar 435=First Sensed in Left Atrium (A2)

In histograms 425 and 440, bar 430 indicates the percentage of AFL/AF events first sensed in the right atrium (40%), while bar 435 indicates the percentage first sensed in the left atrium (60%). Thus, the biatrial sensing allows for the determination of the originating chamber of various atrial arrhythmias, which then allows for an optimization of therapy.

Once it has been determined which chamber the AFL/AF is occurring in, the particular therapy can be implemented. For atrial flutters, the first therapy would be to overdrive the chamber. If unsuccessful, the next choice of therapy would be cardioversion. For atrial fibrillation, defibrillation is the appropriate therapy. Again, by targeting the originating chamber, therapy can be delivered to that chamber directly. The localization of the problem through the above data allows for a determination of the best chamber to implement the therapy. The therapy can be determined by a cardiologist observing the data, or automatically implemented by IMD 10, once the problem has been appropriately identified.

Figure 13A:
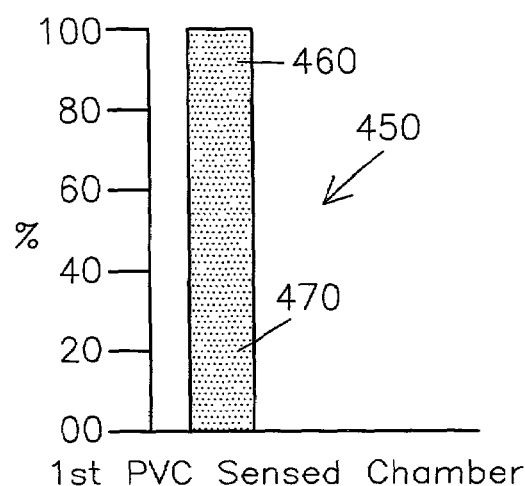
FIGS. 13A and 13B are sample histograms illustrating a determination of the origin of premature ventricular contractions.
Figure 13B:
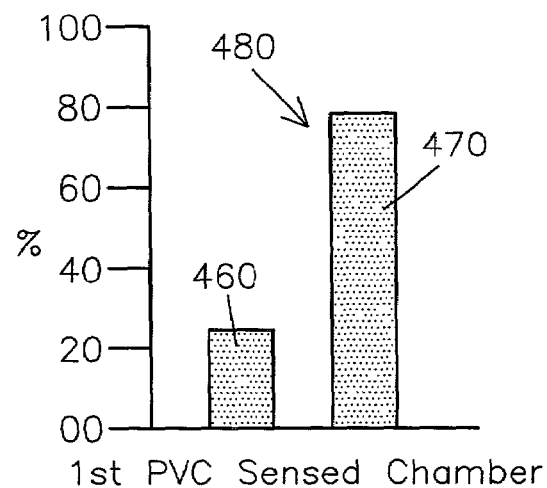

Biventricular sensing allows for the determination of the origin of various ventricular arrhythmias. FIGS. 13A and 13B represent sample data indicating which ventricular chamber first sensed a premature ventricular contraction (PVC). That is, by having a sensing lead located both in the right ventricle (V1) and the left ventricle (V2), data is recorded indicating which of these leads first sensed the PVC.

For this example, the sensed PVC break down is as follows:
Bar 460=First Sensed in Right Ventricle (V1)
Bar 470=First Sensed in Left Ventricle (V2)

Histograms 450 and 480 include bar 460 that indicates 24% of the detected PVC's started in the right ventricle, while bar 470 indicates that 76% of the detected PVC's started in the left ventricle. Once it has been determined where the problem is originating, the therapy can be tailored to address it.

This data will help the cardiologist determine the nature of the PVC's that are occurring. If they are fairly infrequent, ATP can be utilized to attempt to solve the problem. If frequent, the data can help the cardiologist locate the ischemia. Once identified, a surgical bypass may be performed to deliver a greater blood flow. Alternatively, local ablation (such as radio frequency or RF ablation) can be performed to destroy the focus that is repetitively firing.

Figure 14A:
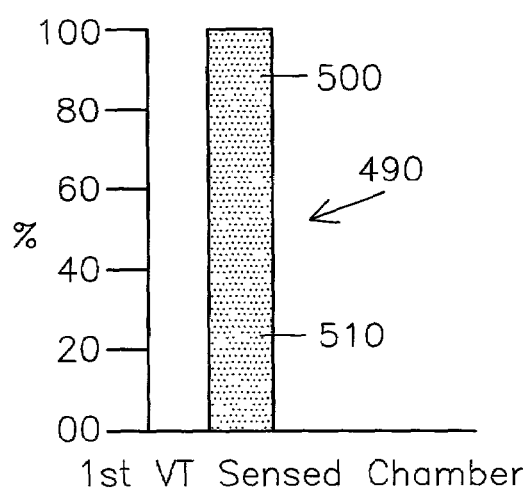
FIGS. 14A and 14B are sample histograms illustrating a determination of the origin of ventricular tachycardia.
Figure 14B:
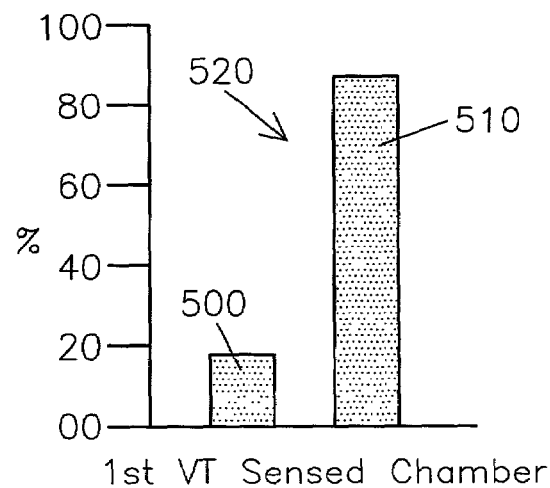

FIGS. 14A and 14B represent sample data determining the origin of ventricular tachycardia (VT). For this example, the sensed VT break down is as follows:
Bar 500=First Sensed in Right Ventricle (V1)
Bar 510=First Sensed in Left Ventricle (V2)

Histograms 490 and 520 represent the same data. Bar 500 indicates that 16% of the sensed VTs started in the right ventricle, while bar 510 indicates that 84% started in the left ventricle. Thus, it is apparent that the VTs for this patient predominantly start in the left ventricle.

This data will indicate which chamber is predominantly having VT's. If they are not too fast, the appropriate therapy will be ATP. If that does not work or is inappropriate the secondary therapy is cardioversion with a triggered electric shock. Of course, by knowing which chamber the problem is originating in, therapy can be delivered directly to that chamber (or to both with biventricular pacing). The therapy can be determined by a cardiologist observing the data, or automatically implemented by IMD 10, once the problem has been appropriately identified.

The present invention can utilize biatrial and/or biventricular sensing and/or pacing leads on an IMD 10 to gather information relating to the patient's cardiac condition. This data is generally stored within a memory of the IMD 10 and later extracted for analysis. The above description provides sample data for some of the conditions, indications and situations determinable with this configuration. These examples are not meant to be exhaustive or limiting. In addition to gathering data, particular therapies can be determined and implemented by a medical professional, and in some case automatically implemented by IMD 10. Such therapies can include surgical ablation, surgical bypass, ATP, cardioversion and defibrillation.

Figure 15:
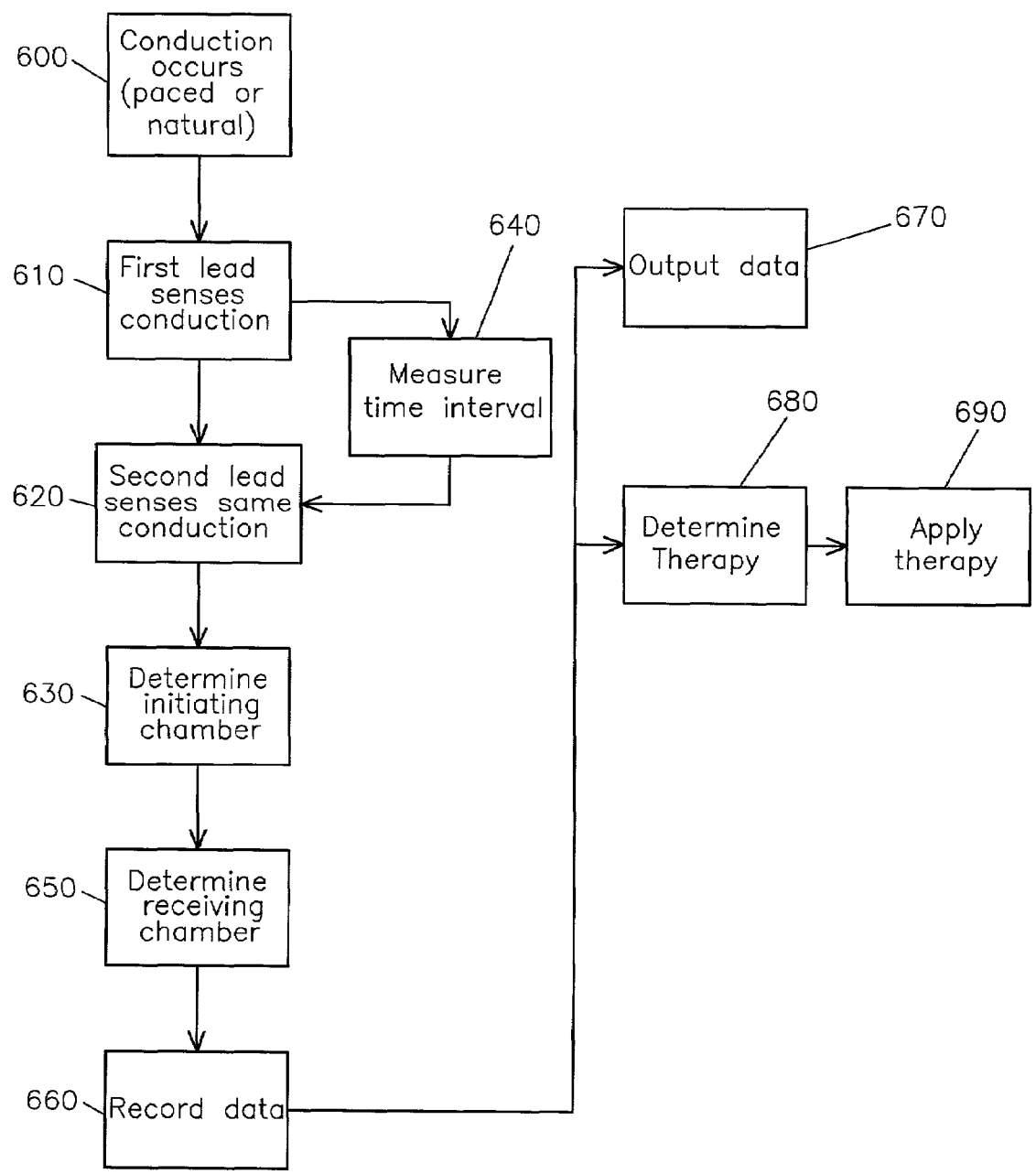
FIG. 15 is a flowchart illustrating the process of determining conduction sequences with the pacing system of the present invention.

FIG. 15 is a flowchart illustrating how IMD 10 can be utilized to determine and react to various conduction sequences. As explained above, the originating and receiving chambers of each conduction can be determined and this information can be recorded for subsequent use. The conductions can occur naturally or can be the result of pacing. In either case, a conduction occurs (600) within the patient's heart 8. That conduction will be sensed by a first lead (610). Alternatively at (610), the first lead could initiate the conduction via pacing rather than first sensing a natural conduction. Some time later, a second lead in a different chamber will sense the same conduction. (620). If this is a natural conduction, the originating chamber is determined (630) based on which lead first senses the event. This information will already be known in the pacing context. The receiving chamber is also determined (650) based on which lead subsequently senses the conduction. This data is then recorded (660) in memory within IMD 10.

In some cases, this is all the information that is required. That is, this will indicate the number of conductions occurring from one chamber to another. As explained above, this can include atrial to ventricular, atrial to atrial, and ventricular to ventricular. However, in some contexts it may also be desirable to know the timing of the measured conductions. Thus, the time interval between when the first lead senses (or paces) the conduction and when the second lead senses that conduction is measured (640). This timing data is also recorded (660).

When desired, the recorded data is output (670) through telemetry or other appropriate mechanisms so that it can be analyzed by the cardiologist. The above described histograms represent one format in which the data can be presented to illustrate the conductions that have been recorded.

If appropriate, particular therapies can be identified (680) and applied (690) to the patient based on the recorded data. This can either occur through the implementation of a specific therapy as prescribed by a cardiologist (or other medical professional) analyzing the output data, or it can be a therapy determined by and delivered by IMD 10 based on protocols stored therein.

Figure 16:
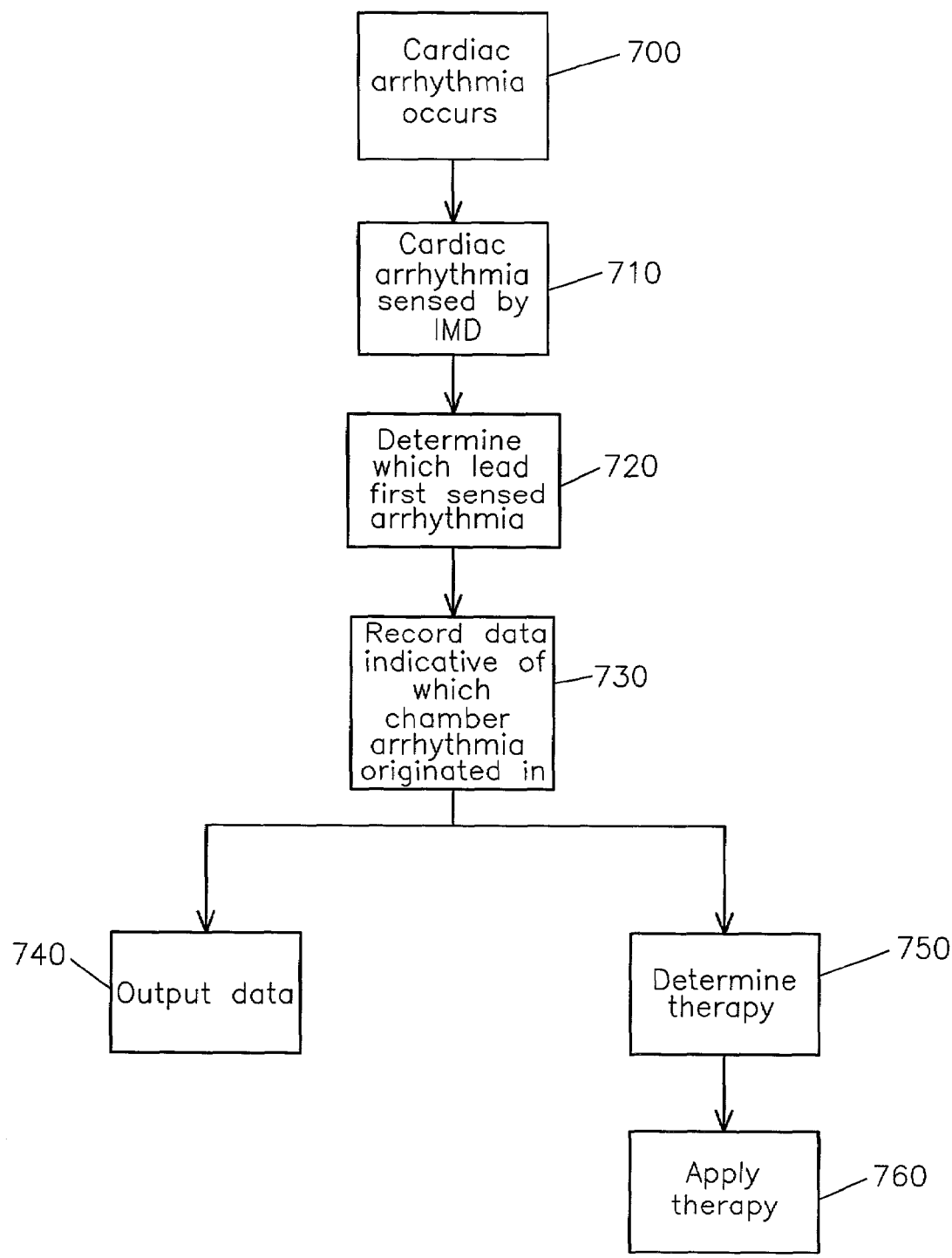
FIG. 16 is a flowchart illustrating the process of determining the originating chamber of various cardiac arrhythmias with the pacing system of the present invention.

FIG. 16 is a flowchart illustrating how IMD 10 can determine and react to various cardiac arrhythmias. At some point in time, a cardiac arrhythmia occurs (700). Examples of the types of arrhythmias sensed would include supra ventricular tachycardias, atrial flutter, atrial fibrillation, premature ventricular contractions or ventricular tachycardias. When an arrhythmia occurs, it is sensed by IMD 10 (710). Because IMD 10 has sensing/pacing lead located in three or four of the chambers, the chamber within which the arrhythmia originated in can be determined (720). This is done by identifying which lead first sensed the arrhythmia. This data is them recorded in memory (730). The data can be output (740) and analyzed by a cardiologist, as described above. The data may simply be informative, or it may indicate that a particular therapy should be applied. The appropriate therapy is determined (750) and applied (760), as described above. This can be done by the cardiologist. Alternatively, where appropriate, the data may indicate that IMD 10 should deliver a specific therapy immediately or as a course of regular treatment. For example, should an AFL/AF be detected, IMD 10 could react by delivering antitachycardia pacing, a cardioversion shock or defibrillation, as appropriate.

The preceding specific embodiments are illustrative of the practice of the invention. It is to be understood, therefore, that other expedients known to those skilled in the art or disclosed herein may be employed without departing from the invention or the scope of the claims. For example, the present invention is not limited to sensing or determining the origin of specific conditions or indicators. Rather, the present invention can be employed to gather a wide variety of different types of information on any number of conditions or indicators. The present invention further includes within its scope methods of making and using biatrial and/or biventricular sensing and/or pacing configurations with data collection, as described hereinabove.

In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. A method of utilizing a biventricular pacing system to determine the distribution of ventricle to ventricle conduction sequences in a patient having a conductive disorder, the method comprising:
    placing sensing leads in both ventricular chambers;
    sensing conduction sequences occurring from one ventricular chamber to another ventricular chamber;
    determining which ventricular chamber the conduction sequence originated in and which ventricular chamber it propagated to;
    recording the determining information in a memory such that the information can be used to identify the relative distribution of conduction sequences;
    identifying a conductive disorder in response to the determined relative distribution; and
    adjusting a therapy delivered by the pacing system in response to the identified conductive disorder, wherein the conductive disorder comprises a conductive disorder amenable to termination via anti tachycardia pacing (ATP) therapy delivery and wherein the therapy comprises ATP therapy and the adjusting further comprises: initiating the ATP therapy in the ventricular that one of: initiated a recent ventricular depolarization and initiated a majority of ventricular depolarizations over a predetermined time period.

2. The method of claim 1, further comprising:
    measuring the temporal dimension from the beginning to the conclusion of a plurality of prior conductive sequences; and
    storing the measured information in the memory by a range of said temporal dimensions so that the measured information can be utilized to select and adjust the anti tachycardia pacing therapy based on at least one recently measured temporal dimension.

3. The method of claim 2, wherein each measured conductive sequence increments a unit counter representing one of a plurality of temporal dimensions.

4. The method of claim 2, further comprising:
    pacing one ventricular chamber in order to generate a conductive sequence.

5. A biventricular pacing system for determining the distribution of conduction sequences from a first ventricle (V1) to a second ventricle (V2) in a patient having a conductive disorder, comprising:
   sensing means located in both ventricular chambers (V1, V2) for sensing conduction sequences occurring from one ventricular chamber to another ventricular chamber;
   means for determining which ventricular chamber the conduction sequence originated in and which ventricular chamber it propagated to;
   means for recording the determined information in a memory such that the information can be used to identify the relative distribution of conduction sequences; and
   means for detecting an arrhythmia susceptible to termination via anti tachycardia pacing (ATP) therapy and adjusting the ATP therapy based at least in part upon the ventricular chamber the arrhythmia originated in.

6. The biventricular pacing system of claim 5, further comprising:
   means for measuring the timing of each conductive sequence and including the measured timing information in the memory to identify relative timing information correlated to the distribution of the conduction sequences.

7. The biventricular pacing system of claim 6, wherein each measured conductive sequence increments a counter representing one of a plurality of discrete time ranges indicative of the timing of the conductive sequence.

8. The biventricular pacing system of claim 6, further comprising:
   means for pacing one ventricular chamber in order to generate a conductive sequence.

9. The biventricular pacing system of claim 8, wherein each measured conductive sequence is caused to increment a counter representing one of a plurality of time ranges indicative of the timing of the paced conductive sequence.

10. The biventricular pacing system of claim 5, further comprising:
    means for delivering anti tachycardia pacing in response to the determined information, wherein the determined information includes arrthymia propagation information.

11. A biventricular pacing system according to claim 10, wherein said arrthymia propagation information includes at least one of the following characteristics: an arrhythmia type, an arrhythmia-propagation interventricular direction code (e.g., "V1–V2" or "V2–V1").

12. A biventricular pacing system according to claim 11, wherein said arrhythmia type includes a ventricular fibrillation code.

13. A biventricular pacing system according to claim 11, wherein said arrhythmia type includes a ventricular tachycardia code.

14. A biventricular pacing system according to claim 11, wherein said arrhythmia type includes a pre-ventricular contraction (PVC) code.

15. A biventricular pacing system according to claim 11, wherein said arrhythmia type includes an ectopic foci code.

16. A biventricular pacing system according to claim 11, wherein the arrhythmia-propagation interventricular direction code is used to determine in which ventricle the anti tachycardia pacing is initiated.

17. A biventricular pacing system according to claim 10, wherein arrhythmia propagation interventricular direction (e.g., "V1–V2" or "V2–V1") further comprises a histogram of at least one prior arrhythmia episode.

18. A biventricular pacing system according to claim 10, wherein said anti tachycardia pacing (ATP) comprises one of a first delivery of ATP and a second delivery of ATP.

* * * * *